United States Patent [19]
Gross

[11] Patent Number: 5,843,048
[45] Date of Patent: Dec. 1, 1998

[54] EPIDURAL CATHETER NEEDLE

[75] Inventor: James R. Gross, Wareham, Mass.

[73] Assignee: The Kendall Company, Mansfield, Mass.

[21] Appl. No.: 692,556

[22] Filed: Aug. 6, 1996

[51] Int. Cl.$^6$ .................................................. A61M 5/32
[52] U.S. Cl. ............................ 604/264; 604/51; 604/272
[58] Field of Search ..................................... 604/264, 272, 604/44, 49, 51, 169, 170, 158, 164

[56] References Cited

U.S. PATENT DOCUMENTS

| | | | |
|---|---|---|---|
| 4,490,139 | 12/1984 | Huizenga et al. | 604/264 X |
| 4,689,040 | 8/1987 | Thompson | 604/272 X |
| 4,721,506 | 1/1988 | Teves | 604/51 |
| 5,207,658 | 5/1993 | Rosen et al. | 604/272 |

*Primary Examiner*—John D. Yasko
*Attorney, Agent, or Firm*—David J. Koris

[57] ABSTRACT

An epidural needle through which an epidural catheter may be threaded for administering liquid anesthesia into the epidural space, the needle having a curved distal end, the tip of the needle distal to the opening in the needle shaft being substantially planar at an angle of 80°–100° relative to the curved longitudinal axis of the needle shaft, the needle tip being characterized as being faceted so as to retard inadvertent passage of the needle tip through the dura mater of a patient while at the same time retaining the sharp cutting edges common to a like epidural needle which has not had its tip so treated.

8 Claims, 5 Drawing Sheets

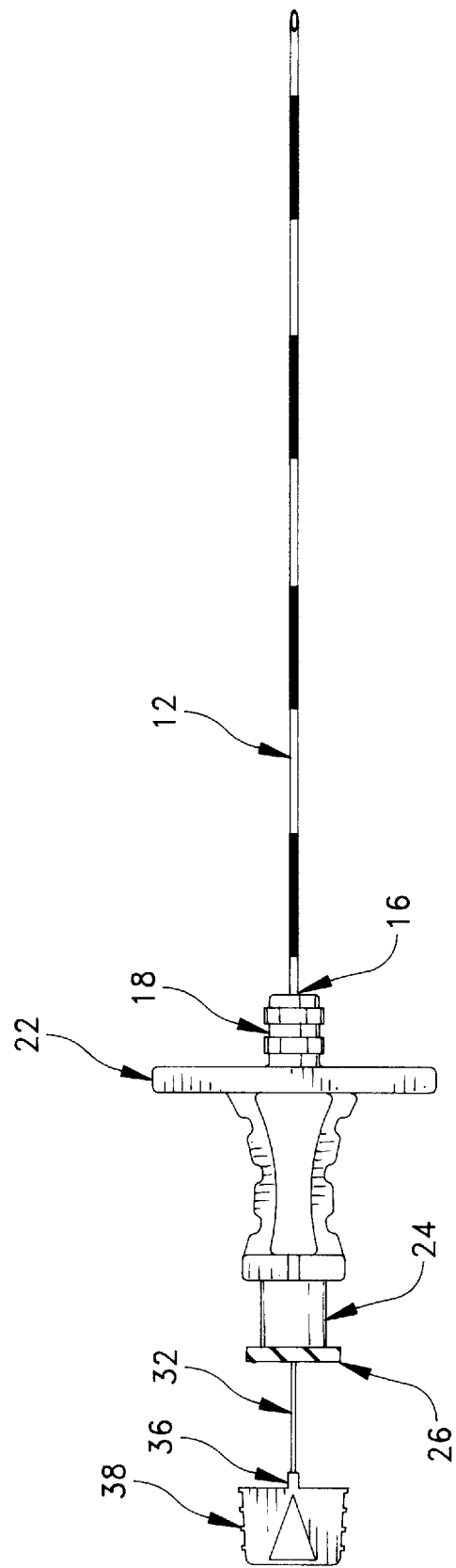

EPIDURAL CATHETER NEEDLE

BACKGROUND OF THE INVENTION

In general there are two methods for administering epidural anesthesia. The first is by means of a straight epidural needle connected at its proximal end to a syringe or other source of liquid anesthesia. The second is by means of a curved tip epidural needle used to introduce an epidural catheter into the epidural space, which ranges on the order of 2–7 mm in width.

The present invention is directed to the latter.

Straight epidural needles employed in the former procedure do not require the passage of a catheter. They typically have a straight distal end and a gauge size on the order of 21–22 gauge (iso-9626); while those of the latter type, through which a catheter is introduced, of necessity are somewhat larger, having a gauge size typically on the order of 17–18 gauge (iso-9626).

The needles of the latter type, used for introducing a catheter into the epidural space, possess a curved tip so that the distal end of the catheter can curve upward for proper placement within the epidural space rather than perpendicularly abutting the dura mater, the delicate membrane lying over the arachnoid and pia mater covering the spinal cord.

The epidural needles of the curved type currently in use are of two kinds: (1) those curved to have an inclined surface on the order of 7° from the longitudinal axis known as "Tuohy" epidural needles; and (2) those curved to have an inclined surface on the order of 12° from the longitudinal axis known as "Husted" epidural needles.

Whether the procedure is of the former type wherein the anesthesia is introduced through a syringe attached to the epidural needle or of the latter type where the anesthesia is introduced through a catheter, great care must be taken to avoid puncturing the dura mater which would permit spinal fluid to leak out.

In a typical procedure to which this invention is directed, the patient, having been prepped for surgery, is brought into an induction room adjacent the operating room where the anesthesiologist is to insert the epidural catheter in preparation for surgery. A local injection may first be given to minimize pain and discomfort from the epidural needle. With the stylet in the needle, the needle is slowly and carefully inserted until it abuts the ligamentum flavum, at which time the skilled hands of the anesthesiologist senses an increase of resistance to further insertion. At this time, the stylet is removed from the needle and a "loss of resistance" syringe is attached to the luer fitting of the needle hub. By slowly advancing the needle and syringe while simultaneously applying pressure to the syringe piston, the ligamentum flavum is penetrated and the needle advanced into the peridural space where loss of resistance to the syringe piston is confirmed.

At this point, the syringe is removed and the epidural catheter is inserted through the needle until the distal end of the catheter exits the curved tip of the needle and is inserted the desired distance into the peridural space.

The proximal end of the catheter is then placed in fluid communication with a source of the anesthetic drug to be introduced. Typically, this is done by securing the proximal end of the catheter within the distal end of an adapter and securing a syringe containing the anesthetic drug to the proximal end of the adapter.

U.S. Pat. No. 4,721,506 issued to Teves Jan. 26, 1988 is believed to be the most relevant prior art to the present invention which will be discussed subsequently.

The Teves patent is directed to the former epidural procedures employing a straight tip needle for introducing an anesthetic drug by means of a syringe directly into the peridural space.

As disclosed therein and defined, for example, in patent claims 3 and 4, an epidural needle with an inclined surface of 40° to 50° relative to the longitudinal axis and having a shaft of approximately 22 gauge is ground to provide a rounded and blunted tip comprising about 30% of the diameter of the needle and forming an angle of about 90° relative to the longitudinal axis of the needle shaft. [For the tip to comprise 30% of the needle diameter, the grinding must of necessity grind away a portion of the distal opening of the needle shaft.] This style epidural needle includes, in combination with the needle shaft, a solid rod (stylet) slidably received in the axial channel of the needle shaft and whose distal end is also rounded and blunted. The needle shaft and the solid rod (stylet) are ground simultaneously and together result in a smooth, rounded, blunted end face with a smooth incline to define a unitary tip configuration. As stated in Col. 6 of the Teves patent, the blunted surface of the unitary tip must be completely rounded to insure that during penetration the needle tip minimizes tissue injury.

As further stated in Col. 6, it is believed that the inclined portion of the unitary tip consisting of the needle shaft and the tip of the solid rod exiting the axial channel of the needle shaft forms a wedge to aid in the transversal of the spinal ligaments while the blunted (and rounded) portion acts as a plow, pushing the veins, arteries and nerves away from the path being traversed.

In use, after placement of the needle in the epidural space, the solid rod (stylet) is removed and a syringe is connected to the needle by means of a luer fitting attached to its proximal end for administration of an anesthesia agent.

The present invention is directed to a similar task to the Teves patent in the sense that both the patent and the instant application are directed to the task of preventing inadvertent penetration of an epidural needle through the dura mater and into the subarachnoid space, causing spinal fluid to leak out.

However, as stated earlier, while the Teves patent is directed to the smaller, straight epidural needles for attachment directly to a syringe for administering the anesthesia, the present invention is directed to the larger curved epidural needles through which a catheter is introduced into the epidural space for administering anesthesia; and the task of the present invention is solved in an entirely different way providing advantages of the teachings of Teves which will be detailed hereinafter.

Furthermore, as will be discussed in detail hereinafter, a direct application of the Teves geometry to a 17 or 18 gauge curved tip needle (not contemplated by the patent) would render that needle useless when attempting to transverse the spinal ligaments.

BRIEF DESCRIPTION OF THE INVENTION

In accordance with the present invention, the task is solved by carefully removing the leading edge of the needle tip to provide an essentially flat or planar point or facet distal to the opening of the lumen or channel within the needle shaft. The solid rod or facet is not affected by this process.

The blunting is accomplished with a precision grinding wheel to remove less than 0.10% of the diameter of the needle and preferably on the order of 0.05% of the diameter. The facet is then buffed in such a manner as to round the facet from top to bottom rather than from side to side, as described in the Teves patent.

BRIEF DESCRIPTION OF THE DRAWINGS

FIG. 6 is a top plan view of the needle of this invention with the solid rod partially removed from the needle shaft.

DETAILED DESCRIPTION OF THE INVENTION

As was mentioned previously, there are two types of needles for use today in administering anesthesia into the epidural space: (1) a needle with a straight shaft for administering the anesthesia from a syringe connected to the proximal end of the needle through a luer fitting; and (2) a needle having a curved distal end for use in introducing a catheter within the epidural space, after which the needle is removed and anesthesia from a syringe is transmitted through the catheter into the epidural space of the patient. The former type needles are on the order of 21–22 gauge; while the latter type are larger, e.g. on the order of 17–18 gauge, in order to accommodate insertion of a catheter within the lumen of the needle shaft. The distal end is curved in order to direct the tip of the catheter away from the dura mater so that it may be inserted the desired distance within the epidural space.

The invention may best be understood by reference to the following detailed description taken in conjunction with the accompanying drawings.

Figure 1:
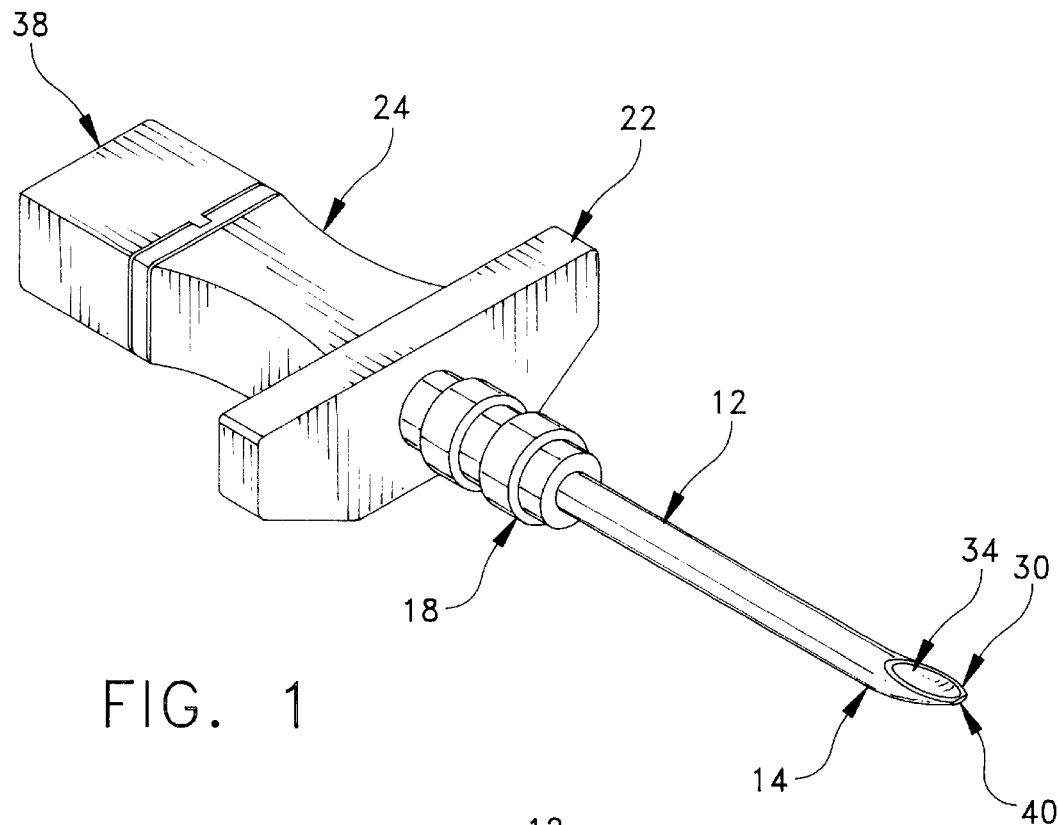
FIG. 1 is a perspective view, greatly enlarged, illustrating the blunted needle of this invention.
Figure 1A:
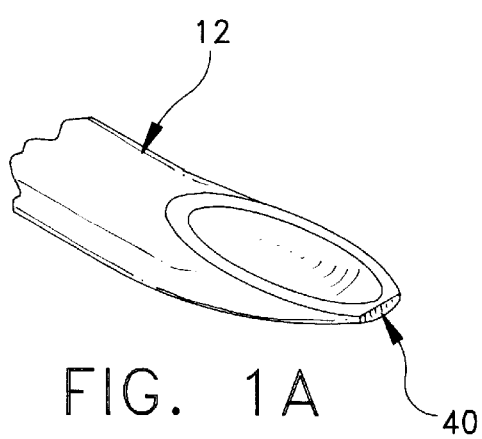
FIG. 1A is an enlarged fragmentary view of the tip of the needle of FIG. 1.
Figure 2:
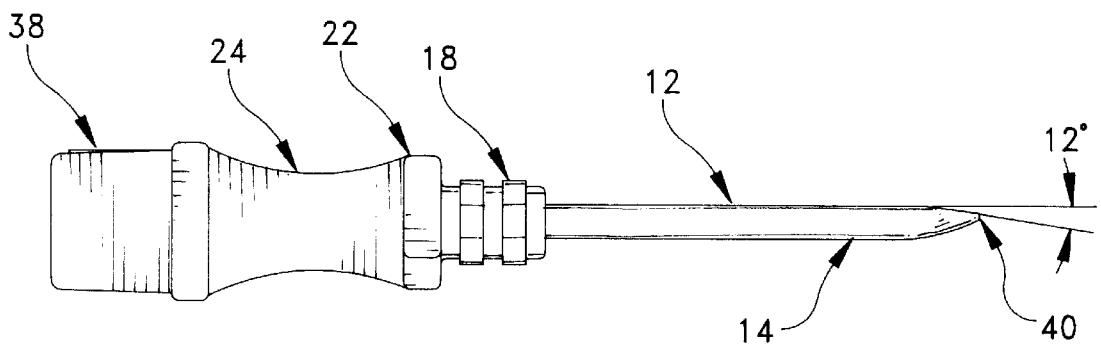
FIG. 2 is a side elevational view of the needle of FIG. 1.

With reference in particular to FIGS. 1–3 and 6, the epidural needle (10) of this invention has a shaft (12), the distal or leading end of which (14) is curved as seen in FIG. 2. The proximal end (16) of the shaft (12) is permanently secured to the distal end (18) of a hub (20) of known configuration having a guide bar (22) for gripping to facilitate introduction and withdrawal of the needle by the anesthetist or other clinician administering the anesthesia.

Figure 3:
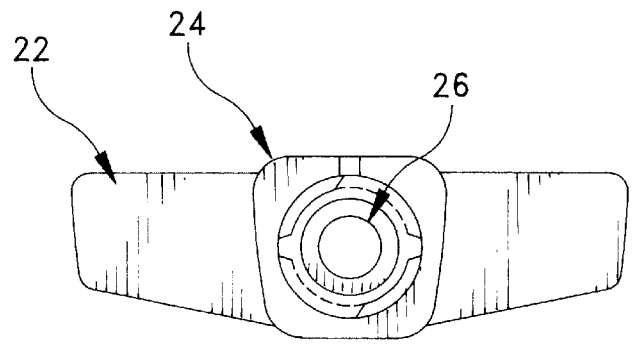
FIG. 3 is a rear view of the needle of FIG. 1 with the solid rod removed.

The proximal end of the hub 24 is provided with a luer fitting (26) as seen in FIG. 3 for securing the needle (10) to a loss of resistance syringe as described earlier in the procedure prior to introducing the catheter through the needle.

As is well understood, the hub has a lumen (not shown) extending between the proximal and distal ends of the hub and which is in fluid communication with the lumen (28) in the needle shaft.

As illustrated in FIGS. 1, 2 and 6, the needle is provided with a solid preferably semi-rigid plastic stylet (32) which is insertable through the luer fitting (26) at the proximal end of the hub (20) until the hub (38) to which the proximal end of the stylet (32) is secured abuts the proximal end (24) of the hub (20) (as seen in FIGS. 1 and 2), at which time the proximal end (34) of the solid stylet (32) extends to the opening (30) at the distal end of the lumen (28) in the needle shaft.

The stylet (32) performs its per se known function with epidural needles, namely to prevent body tissue from blocking or clogging the lumen (28) during penetration of the needle through the tissue of the patient. After the needle has penetrated the tissue, the stylet has of course served its function and may then be removed, simply by grasping hub (38) and retracting.

The foregoing discussion describes a per se known curved epidural needle, e.g. one curved at its distal end (14) at an angle of 5°–15° relative to the longitudinal axis of the needle shaft, as illustrated in FIG. 2.

The essence of the present invention and what may be termed the exact point of novelty is the concept of blunting the tip of the needle, not in the manner described in the aforementioned Teves patent, wherein a rounded tip configuration is provided comprising about 30% of the diameter of the needle and which will then cut off a portion of the rod and opening in the needle, but instead to provide a flat tip (40) at an angle of on the order of 80°–100° to the longitudinal axis of the needle shaft, as seen in FIG. 1.

In accordance with the present invention, the blunted tip (40) will be distal to the opening (30) of the lumen (28) and will comprise less than 0.10% of the diameter of the needle and most preferably on the order of 0.05% of the needle diameter.

Figure 4:
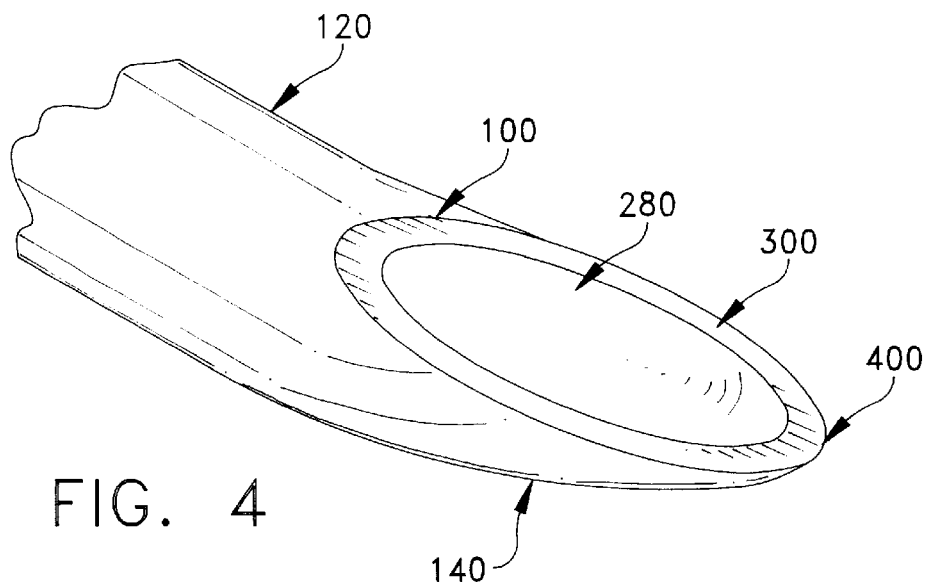
FIG. 4 is a fragmented view illustrating the distal end of an epidural needle of the prior art for use with an epidural catheter for administering anesthesia.
Figure 5:
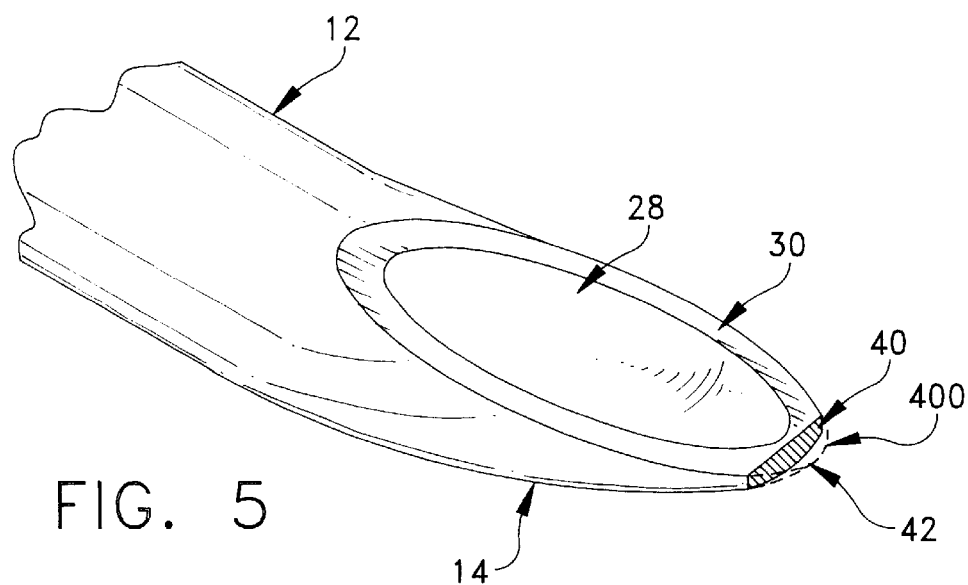
FIG. 5 is a fragmented view similar to FIG. 4 of the epidural needle of this invention showing in dotted lines the portion of the tip of the prior art needle ground away in accordance with this invention.
Figure 5A:
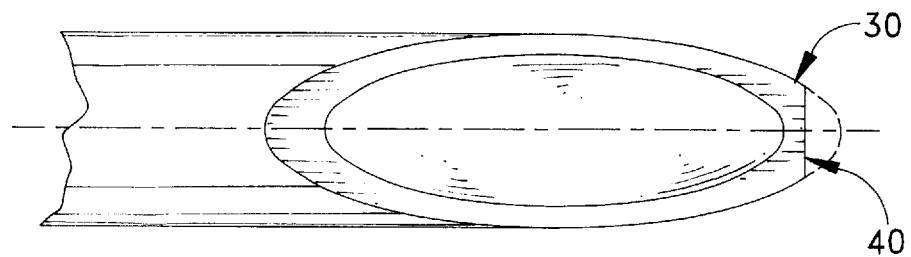
FIG. 5A is an enlarged, fragmentary top elevational view of the blunted tip of this invention showing the nominal amount of material removed during the blunting process.
Figure 5B:
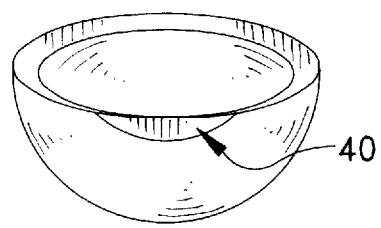
FIG. 5B is a front elevational view showing the blunt facet at the tip on the needle as a result of the blunting process.

With reference to FIGS. 4 and 5, the desired blunting of the needle tip may be accomplished by taking a standard Tuohy needle (120) and removing a portion (42) of its tip (400) as shown by the dotted lines in FIG. 5. This removal may be accomplished with a precision grinding wheel of known type, after which the tip may and most preferably will be subjected to two or three buffing steps. By way of illustration, with an 18 gauge Tuohy needle, approximately ½ of the tip width may be ground off in this manner, removing on the order of 0.003 inch of the 0.053 inch diameter of the needle which equals 0.05% of the needle diameter.

The blunt epidural needle of this invention may then be employed in per se known manner.

After the needle is inserted until it abuts the ligmentum flavum, the stylet (32) is removed, and the needle connected to a loss of resistance syringe, as described earlier, the needle is advanced into the epidural space. At this point, the syringe is disconnected from the needle and the anesthetist is now ready to insert the catheter for introducing anesthesia into the epidural space, as will now be described.

Figure 7:
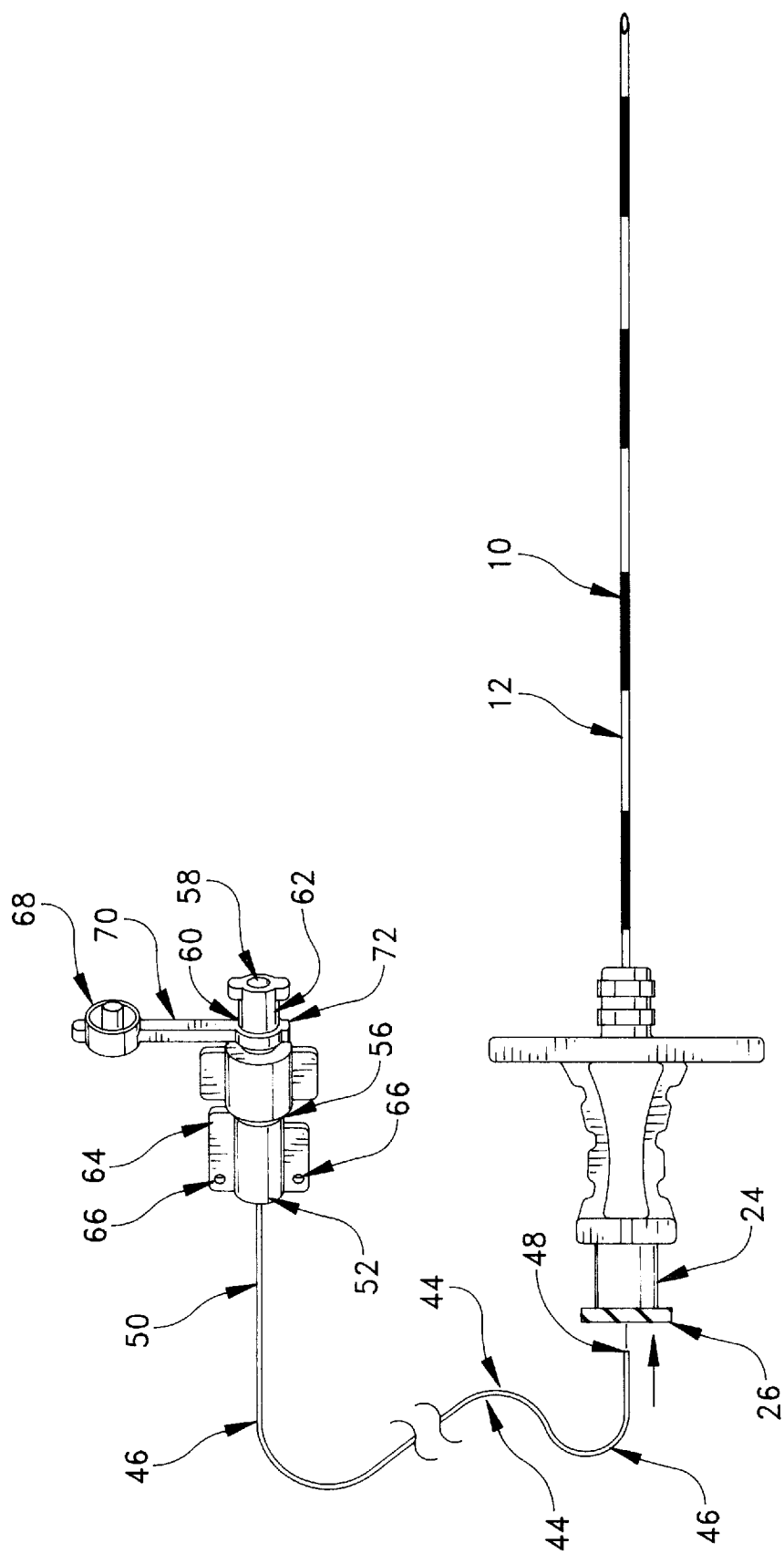
FIG. 7 is a schematic view illustrating the use of the epidural needle of this invention in combination with an epidural catheter to administer anesthesia.

With reference to FIG. 7, a catheter (44) is shown to comprise a cannula (46) having opposed distal and proximal ends (48) and (50) respectively. The Distal end (46) is inserted within the proximal end (24) of the needle hub (20) and advanced until the proximal end of the cannula is inserted the desired distance within the epidural space. The needle is then carefully withdrawn from the patient over the catheter.

The proximal end of the catheter (50) is releasably secured to the distal end (52) of an adapter (56) having a hollow bore (58) extending from the distal end (52) to the proximal end (60) of the adapter. The proximal end of the adapter has a syringe port or luer fitting (62) for securing the adapter to a syringe or other source of liquid anesthesia. While not essential, the adapter (56) is preferably provided with a finger grip flange (64) having holes (66) for securing the adapter to the patient's gown or other item and a cap (68) fitable within the syringe port (62), the cap (68) being secured to the adapter by linkage (70) and retaining ring (72). The purpose of the cap, of course, is to close off the syringe port when not in use administering anesthesia.

Prior to the present invention, the line of epidural needles manufactured and sold by the Kendall Healthcare Products Company division of The Kendall Company, assignee of this application, included three types of curved epidural needles for use with epidural catheters: (1) a "Standard" 18 gauge Tuohy catheter needle which during its manufacture receives two tip buffs; (2) a "Dull" 18 gauge Tuohy catheter needle which receives two longer tip buffs; and (3) a "Superdull" 18 gauge Tuohy catheter needle which receives a sand blast plus two buffs.

The purpose of having three epidural needles for use with an epidural catheter is to provide three ranges of cutting sharpness to accommodate the individual whim or choice of the anesthetists using these needles.

The sharpness of the needle is calculated by a test procedure in which the force in grams required to puncture a surface with the needle is measured by the so-called "2 mil poly test" in which a 2 mil thick sheet of polyethylene is stretched and secured between two upright circular tubes over a lab bench. The test needle is secured vertically above the sheet of polyethylene and the force in grams required to puncture through the sheet is measured with a standard Instron test device, e.g. a model 5564 Instron.

In this manner, Kendall has set the following sharpness requirements for the three classes of epidural catheter needles:

| (1) Standard | 60–80 grams of force |
| (2) Dull | 85–100 grams of force; and |
| (3) Superdull | 100–125 grams of force. |

The following analytical test data compares: (1) Standard Kendall 18 gauge Tuohy needle; (2) Blunt needle of this invention, 2 buffs; (3) Blunt needle of this invention, 3 buffs; and (4) 18 gauge Tuohy needle blunted according to the teachings of Teves U.S. Pat. No. 4,721,506.

The blunt needles of this invention were prepared in the manner heretofore described, namely by grinding 0.003–0.005 inch off the tip of the Standard Tuohy needle with a precision grinder and than giving 2 or 3 buffs.

The blunted needle according to the Teves patent was prepared at The Kendall Company Model Shop by blunting an 18 gauge Tuohy "Standard" needle according to the patented design, grinding to obtain a rounded and blunted tip comprising 30% of the needle diameter.

The four needles thus prepared were tested for sharpness according to standard protocol using the "2 mil poly" test previously described and obtaining the grams of force with a 5564 model Instron. In this test, 30 needle samples were used for each of the three Kendall products and, because of the difficulty in making, only three needle samples of the Teves design were made.

In any case, it is clear that the data generated may be more accurate and therefore more meaningful than if but a single prototype of each class of needles were tested.

These results are set forth in the following Table.

TABLE

| | KENDALL STANDARD TIP, 2 BUFFS | KENDALL BLUNT TIP 2 BUFFS | KENDALL BLUNT TIP 3 BUFFS | TEVES BLUNT TIP |
|---|---|---|---|---|
| MEAN | 46.02 GMs. | 73.71 GMs. | 78.71 GMs. | 212.21 GMs. |
| * SD | 6.34 GMs. | 10.26 GMs. | 9.20 GMs. | 16.27 GMs. |
| HIGH | 67.00 GMS. | 100.30 GMs. | 100.68 GMs. | 229.30 GMs. |
| LOW | 38.27 GMs. | 50.56 GMs. | 60.14 GMs. | 196.92 GMs. |
| GAUGE SIZE | 18 | 18 | 18 | 18 |

* STANDARD DEVIATION

The data in the chart indicates that the Kendall Blunted Tip with two buffs is 59.6% duller than the Standard needle; while the Kendall Blunted Tip with three buffs is 71.% duller than the standard needle. The three buff is in turn 7.16% duller than the two buff.

From the foregoing test results, it will be seen initially that the blunted Kendall needles are within the sharpness ranges previously established for the Dull and Superdull needles. In other words, the blunted needles of the present invention retains the same sharp cutting edges around the periphery of the opening while maintaining essentially the same grams of force to inhibit the blunted tip from cutting through the dura mater. Stated another way, as distinguished from the "dulled" needles the Kendall Healthcare Products Company has previously commercialized, the instant invention provides needles which retain sharp cutting edges giving the anesthetist a more comfortable and easier "feel" for cutting through the tissues while maintaining the same or substantially the same resistance against penetrating the dura mater.

On the other hand, a curved epidural needle contemplated for use in introducing a catheter within the epidural space is rendered useless and perhaps unsafe when blunted in accordance with the geometry and teachings of the aforementioned U.S. Pat. No. 4,721,506 issued to Teves.

From the test data set forth in the above Table it will be observed that the Teves design is 361.1% duller than the Standard Kendall needle; and 169.9% duller than the Kendall Blunt Tip, 3 buff. It was nearly 70% duller than the dullest Tuohy needle the Kendall Healthcare Products Company has commercialized.

Based upon this analytical data, and even allowing for a significant margin of error, it is believed that the sharpness range of the Kendall needle blunted according to the teachings of Teves is so far outside that ranges contemplated by the corporate assignee that in all probability the clinician could not get the needle through the skin of the patient. In any case, it is thought clear that a clinician attempting to use the Tuohy needle incorporating the Teves design would immediately discard it and obtain a different needle.

In so stating this conclusion, it is not intended to pass judgment or deprecate the patented invention which it is stressed is directed to the straight tip epidural needles intended to be used with a syringe to inject anesthesia and which are much smaller and therefore easier to introduce into the body.

What is stressed, however, is that while the Teves design may be perfectly satisfactory for the straight needles to which the invention is in fact directed, it is useless for use with the curved epidural needles contemplated by the present invention.

In accordance with this invention, the anesthesia may be administered in per se known manner. For example, following the procedure previously described, the needle is inserted within the epidural space. The catheter is then threaded through the needle until a desired length of the catheter is within the epidural space, after which the needle is then removed by sliding it over the entire length of catheter, care of course being taken not to dislodge the position of the catheter within the epidural space. After the needle has been removed, the proximal end of the catheter is then secured to the adapter in preparation for the commencement of the administration of anesthesia.

It will be appreciated that various changes may be made with out departing from the spirit of the present invention, the scope of which will be defined in the appended claims.

For example, as shown in FIGS. 6 and 7, to assist the anesthetist in determining the proper distance to insert the needle for a given patient, the needle shaft may be provided with needle depth markings consisting of alternating sections of a different color of a desired uniform length, e.g. one centimeter If desired, each segment may also be numbered consecutively, the number on each segment designating the distance of that segment within the body, as described and claimed in the copending application of the present Applicant, Ser. No. 08/205,230 filed Apr. 4, 1994.

It is also contemplated the present invention is useful in the split needle invention described and claimed in U.S. Pat. Nos. 5,322,512, 5,425,717 and D352,108 wherein the needle may be removed from the catheter by splitting it along the shaft instead of having to slide it over the needle, thereby permitting the proximal end of the catheter to be permanently secured to an adapter.

Other changes and modifications may be readily suggested to those skilled in the art in the light of the foregoing description. Accordingly, it is to be expressly understood that the foregoing description of the invention and the appended drawings shall be taken as illustrative and not in a limiting sense.

What is claimed is:

1. In an epidural needle comprising a hollow shaft having opposed distal and proximal ends, the distal end having a sharp tip for insertion into a patient's epidural space, the needle shaft having a lumen extending from the proximal end of the needle shaft and terminating at an opening proximal to the distal tip of the needle shaft and configured to allow an epidural catheter for introducing liquid anesthesia into the patient to be threaded through the proximal end of the needle until a portion of the catheter exits through the opening in the needle shaft, the distal end of the needle shaft having an inclined surface of at least 5° with respect to the longitudinal axis of the shaft;

the improvement wherein the distal tip of the needle distal to the opening in the needle shaft is substantially planar at an angle of on the order of 80°–100° relative to the longitudinal axis of the needle shaft, the needle tip being characterized as being faceted so as to retard inadvertent passage of the needle tip through the dura mater of the patient while at the same time retaining the sharp cutting edges common to a like epidural needle which has not had its tip so treated.

2. An epidural needle as defined in claim 1 wherein the planar tip of the needle is no more than about 0.10% of the diameter of the needle shaft.

3. An epidural needle as defined in claim 1 wherein the sharpness of the needle tip, as measured by the grams of force required for the needle tip to puncture a sheet of two mil thick polyethylene, is from about 85 grams of force to about 100 grams of force.

4. An epidural needle as defined in claim 1 wherein the sharpness of the needle tip, as measured by the grams of force required for the needle tip to puncture a sheet of two mil thick polyethylene, is from about 100–125 grams of force.

5. An epidural needle as defined in claim 1 wherein the needle is a 17 or 18 gauge needle.

6. An epidural needle comprising:

a hollow shaft having opposed distal and proximal ends, the distal end having a sharp tip for insertion into a patient's epidural space, the needle shaft having a lumen extending from the proximal end of the needle shaft and terminating at an opening proximal to the distal tip of the needle shaft whereby an epidural catheter for introducing liquid anesthesia into the patient can be threaded through the proximal end of the needle until a portion of the catheter exits through the opening in the needle shaft, the distal end of the needle shaft having an inclined surface of at least 5° with respect to the longitudinal axis of the shaft;

the distal tip of the needle distal to the opening in the needle shaft is substantially planar at an angle of on the order of 80°–100° relative to the longitudinal axis of the needle shaft, the needle tip being characterized as being faceted so as to retard inadvertent passage of the needle tip through the dura mater of the patient while at the same time retaining the sharp cutting edges common to a like epidural needle which has not had its tip so treated; and a solid rod having opposed proximal and distal ends, the distance between the opposed ends of the solid rod being substantially the same as the distance between the proximal end of the adapter and the distal tip of the needle shaft, the proximal end of the solid rod being secured to gripping means for holding the rod, the rod being insertable through the proximal end of the adapter such that when the gripping means abuts the proximal end of the adapter, the distal end of the rod extends within the opening in the needle shaft, whereby when inserted within the needle shaft to prevent tissue debris from clogging the lumen during introduction of the needle into the patient's body.

7. An epidural needle as defined in claim 6 wherein the solid rod is made of a semi-rigid plastic material.

8. An epidural needle as defined in claim 1, wherein the inclined surface is inclined at an angle of 5° to 15° with respect to the longitudinal axis of the shaft.

* * * * *